United States Patent [19]

Horwath et al.

[11] 4,011,139
[45] Mar. 8, 1977

[54] PROCESS FOR PRODUCING α-1,6 GLUCOSIDASES USING THERMOPHILIC MICROORGANISMS

[75] Inventors: R. Otto Horwath, Westport; John A. Lally; Philip Rotheim, both of Stamford, all of Conn.

[73] Assignee: Standard Brands Incorporated, New York, N.Y.

[22] Filed: Nov. 26, 1974

[21] Appl. No.: 527,405

[52] U.S. Cl. .................................................. 195/65
[51] Int. Cl.$^2$ ......................................... C12D 13/10
[58] Field of Search ........................... 195/65, 66 R

[56] References Cited

UNITED STATES PATENTS

| | | | |
|---|---|---|---|
| 3,796,635 | 3/1974 | Delente | 195/65 |
| 3,804,715 | 4/1974 | Sugimoto et al. | 195/31 R |
| 3,826,714 | 7/1974 | Suekane et al. | 195/65 X |
| 3,827,940 | 8/1974 | Sugimoto et al. | 195/66 R |

FOREIGN PATENTS OR APPLICATIONS 91,272  11/1973  Japan

OTHER PUBLICATIONS

Biochemical Society Transactions vol. 1, No. 1, p. 266, Jan. 1973.

*Primary Examiner*—Lionel M. Shapiro

[57] ABSTRACT

Thermophilic microorganisms which produce α-1,6 glucosidases are grown under aerobic conditions in an aqueous nutrient medium containing suitable carbohydrate sources. The medium is maintained at a suitable pH and, typically, at a temperature above about 40° C to provide substantial growth of the microorganisms and production of α-1,6 glucosidases.

15 Claims, No Drawings

PROCESS FOR PRODUCING α-1,6 GLUCOSIDASES USING THERMOPHILIC MICROORGANISMS

THE INVENTION

This invention relates to a process for producing α-1,6 glucosidases using thermophilic microorganisms. More particularly, this invention relates to a process for producing α-1,6 glucosidases under aerobic conditions in an aqueous nutrient medium containing suitable carbohydrate sources.

Enzymes which affect the hydrolytic conversion of starch are referred to in the art as amylolytic enzymes or amylases and may be derived from fungal and bacterial sources and from malted cereal grains. A number of different amylases have been identified on the basis of their particular hydrolytic effects on the amylose and amylopectin components of starch. Alpha-amylase hydrolyzes the α-1,4 linkages in both amylose and amylopectin and, in commercial practice, is generally used to liquefy starch to reduce its viscosity. Beta-amylase has a saccharifying effect on starch resulting from its ability to hydrolyze the α-1,4 linkages at the ends of the amylose and amylopectin chains and thus split off maltose units from the non-reducing chain ends. Another amylolytic enzyme, glucoamylase, hydrolyzes starch to glucose. None of the aforementioned amylases, with the exception of glucomylase, can act upon the α-1,6 glucosidic interchain linkages in amylopectin and glycogen or their degradation products.

Amylolytic enzymes which hydrolyze the α-1,6 glucosidic interchain linkages in amylopectin are broadly referred to in the art as α-1,6 glucosidases. A number of enzymes having considerably different specificities have been identified in the art as being capable of hydrolyzing α-1,6 glucosidic interchain linkages. Of these, the two most important enzymes from the commercial standpoint are pullulanase and isoamylase. The major difference in regard to the specificity of these enzymes is that pullulanase will degrade the linear polysaccharide pullulan whereas isoamylase will not to any significant degree.

The majority of the known species of microorganisms are classified as mesophilic, i.e., they require relatively moderate temperatures in the range of from about 20° to 40° C for growth. A number of microorganisms, however, are thermophilic, i.e., they will grow at temperatures above about 40° C. In general, enzymes produced by thermophilic microorganisms are active at temperatures within the range of temperatures which supports the growth of the parent microorganisms.

Although there are a number of patents and publications which disclose the production of enzymes by thermophilic microorganisms, there is little prior art relating to the production of α-1,6 glucosidases by such microorganisms. Japanese Patent Specification NS 91272/73 relates to a process for producing isoamylase by culturing strains of the thermophilic microorganism, *Bacillus stearothermophilus*, at a temperature of 60° C in a culture medium containing starch, amino acids and inorganic salts. In a brief note appearing in *Biochemical Society Transactions*, Vol. 1, No. 1, p. 266 (January, 1973), it is noted that *Bacillus stearothermophilus* (ATCC 7954) and a microorganism identified as 8A produce an enzyme capable of hydrolyzing α-1,6 linkages in dextrins. U.S. Pat. No. 3,827,940 to Sugimoto et al is directed to a process for producing heat resistant α-1,6 glucosidases by culturing non-thermophilic microorganisms of the Lactobacillus and Nocardia genera.

There are a number of problems associated with the production and use of α-1,6 glucosidases elaborated by non-thermophilic microorganisms. In processes for producing such enzymes, relatively moderate temperatures, e.g., generally not exceeding about 40° C, must be employed. Maintaining culture media at moderate temperatures, of course, tends to permit growth of contaminating microorganisms which adversely affect the growth of the desired microorganism and decrease the effective yield of enzymes derived therefrom.

It is the principal object of the present invention to provide a process for producing α-1,6 glucosidases using thermophilic microorganisms.

This object and other objects which will be apparent from the following description may be achieved in accordance with the present invention by growing thermophilic microorganisms which produce α-1,6 glucosidases under aerobic conditions in an aqueous nutrient medium having present a carbohydrate selected from the group consisting of glucose, isomers of glucose, oligomers and polymers containing a glucose moiety and isomers of a glucose moiety and mixtures thereof and maintaining the medium at a suitable pH and temperature to provide substantial growth of the microorganisms and production of α-1,6 glucosidic enzymes.

Since the thermophilic microorganisms of the present invention can be cultivated at relatively high temperatures, the likelihood of infection by contaminating microorganisms which might adversely affect the yield of α-1,6 glucosidases is significantly decreased. Moreover, the enzymes produced by such thermophilic microorganisms are generally heat stable, which results in their being utilizable at relatively high temperatures, thus increasing the rate at which enzyme catalyzed reactions will proceed. In the case of utilizing these α-1,6 glucosidases for debranching of liquefied starch, the performing of such process at high temperatures prevents or lessens retrogradation of the starch, thus resulting in greater yields of starch conversion products and processing economies.

Suitable carbohydrates for use in media for cultivating the thermophilic microorganisms of the present invention are those which contain α-1,4 glucosidic linkages, α-1,6 glucosidic linkages or both. Exemplary of carbohydrates which are contemplated as being suitable for use in the present invention are glucose and isomers of glucose, oligomers and polymers containing a glucose moiety or isomers of a glucose moiety and mixtures thereof including the following: fructose, galactose, allose, starch, methylglucoside, maltose, maltotriose, isomaltose, panose, trehalose, cellobiose, sucrose, maltulose, glucosylxyloside, maltitol, lactose, raffinose, melibiose, sorbose, psicose, maltotetraose, amylose, cellulose, cellulose derivatives, amylopectin, amylopectin derivatives, glycogen, glycogen derivatives, dextran, pullulan, inulin and levan.

The preferred carbohydrates for use in cultivating the microorganisms of the present invention are maltitol, maltose, starch, amylopectin and various mixtures thereof.

The conditions under which the thermophilic microorganisms are cultivated may vary over a relatively wide range depending upon the particular microorganisms used and other factors. Substances such as peptone, tryptone, corn steep liquor, yeast extract and various combinations thereof may be present in the culture medium.

A source of metal ions such as soluble salts of cobalt, calcium, magnesium and the like may also be present in the culture medium to stabilize or activate the α-1,6 glucosidase.

The pH and temperature at which the thermophilic microorganisms may be cultured may also vary over a relatively wide range, but, of course, must be such that will not adversely affect the growth of the microorganisms or the production of the α-1,6 glucosidase. It is contemplated that the microorganisms may be cultured in a pH range of from about 5 to about 8 and preferably in the range of from about 6 to about 7.5. The most preferred pH range is from about 6.4 to about 7.2. Typically, the microorganisms will be cultured at a temperature of above about 40° C and preferably at a temperature in the range of from about 45° to about 70° C. The most preferred temperature range is from about 50° to about 60° C. While some of the microorganisms of the present invention will grow at temperatures below 40° C, all are true thermophiles, showing optimal growth at temperatures above 40° C.

The preferred microorganisms for use in the present process are those belonging to the Bacillus genus, the Actinomycetales order and gram negative rod shaped organisms.

After the thermophilic microorganisms have been propagated, the α-1,6 glucosidase may be recovered from the growth medium by separating the enzyme from other constituents of the medium. Also, the cellular material may be simply removed or separated from the growth medium and this cellular material used as a source of α-1,6 glucosidase.

To evidence the production of α-1,6 glucosidases by the thermophilic microorganism of the present invention, amylopectin or a source of amylopectin was incorporated into the nutrient media in which the microorganisms were grown on agar plates or in liquid broth. Debranching of the amylopectin substrate was shown by the presence of amylose in the media during and following growth of the microorganisms. As a source of amylopectin, any substantially amylose free starch may be used. Substantially amylose free waxy maize starch is preferred.

A visual colorimetric method was used for determining starch debranching enzyme activity of the α-1,6-glucosidases produced by the thermophilic microorganisms of the present invention. This method is based upon the formation of a blue amylose-iodine complex when amylose, which is split off from amylopectin by starch debranching enzymes, reacts with iodine-potassium iodide solution (25 ml of 0.1N $I_2$—KI solution diluted to one liter and 5 ml of concentrated HCl added).

The greater the starch debranching enzyme activity present, the greater will be the intensity of the blue color formed. When the microorganisms are grown in liquid media containing a source of amylopectin, starch debranching activity may be visualized by adding iodine-potassium iodide solution to the contents of the flask in which the microorganism are propagated or a portion of the flask contents may be removed and treated with the solution. Starch debranching activity may be visualized when the microorganisms are grown on agar plates by spraying the iodine-potassium iodide solution onto the surface of the agar medium and observing the areas and intensity of the blue color formed.

In order to more clearly describe the nature of the present invention, specific examples will hereinafter be described. It should be understood, however, that this is done solely by way of example and is intended neither to delineate the scope of the invention nor limit the ambit of the appended claims. In the examples and throughout the specification, percentages are utilized to refer to percent on a weight/volume basis unless otherwise specified.

EXAMPLE I

This Example illustrates the isolation of the thermophilic microorganisms of the present invention from soils, hot springs and other geothermal locations.

Soil samples were screened through a 200 mesh U.S. Standard Screen and approximately one gram of each screened sampled was distributed under aseptic conditions over the surface of autoclaved agar-containing media. For the liquid samples, a small volume of each sample was sprayed on the media in a similar manner. A number of basal media containing a variety of ingredients and concentrations of the same were found suitable for supporting the growth of thermophilic microorganisms present in the samples at a temperature of 55° C. Typical of such media were those having the compositions shown in Table I:

TABLE I

Composition of Media Supporting Growth of the Thermophilic Microorganisms

| Ingredient | Medium A Percent | Medium B Percent |
|---|---|---|
| Waxy maize starch | 0.5 | 0.5 |
| Tryptone | 0.5 | |
| Peptone | | 1.0 |
| Yeast Extract | 0.5 | |
| $CoCl_2 . 6H_2O$ | 0.01 | |
| $CaCl_2 . H_2O$ | 0.01 | |
| $K_2HPO_4 ... 7H_2O$ | | 0.5 |
| $MgSO_4 . 7H_2O$ | | 0.05 |
| KCl | | 0.05 |
| $FeSO_4 .7H_2O$ | | 0.001 |
| $NaNO_3$ | | 0.5 |
| Agar | 2.5 | 2.5 |
| *Maltose | 1.0 | 1.0 |
| pH before autoclaving | (6.7) | (7.5) |

*Autoclaved separately from other ingredients

Inoculum for fresh plates was prepared by suspending in 5 ml. of saline solution one loopful of 3 to 4 day growth from plates on which the thermophilic microorganisms had been cultivated at 55° C. The suspensions were then streaked onto fresh plates containing the agar-containing medium using sterile swabs and the plates incubated at 55° C. for 3 to 4 days. Upon removal of the plates from the incubator, they were sprayed immediately with the iodine reagent. The appearance of blue zones on the treated plates was indicative of the presence of amylose resulting from the activity of α-1,6 glucosidase, produced by the cultured microorganisms, on the amylopectin of the waxy maize starch in the basal medium.

Thermophilic microorganisms isolated by the above procedure which produced α-1,6 glucosidases are those shown in Table II below:

TABLE II

| | Thermophilic Microorganisms Isolated from the Samples | | |
|---|---|---|---|
| ATCC* No. | Genus or Order | Gram Stain | Form |
| 31068 | — | Neg. | Rod |

TABLE II-continued

Thermophilic Microorganisms Isolated from the Samples

| ATCC* No. | Genus or Order | Gram Stain | Form |
|---|---|---|---|
| 31069 | Actinomycetales | Neg. | Rod with branching |
| 31070 | Actinomycetales | Pos. | Rod with branching |
| 31071 | — | Pos. | Rod with terminal spores |
| 31072 | Bacillus | Pos. | Rod |
| 31073 | Bacillus | Pos. | Rod |
| 31074 | Bacillus | Pos. | Rod |
| 31075 | Bacillus | Pos. | Rod |
| 31076 | Bacillus | Pos. | Rod |
| 31077 | Bacillus | Pos. | Rod |

*ATCC is the abbreviation for the American Type Culture Collection, Rockville, Maryland.

The isolated microorganisms were further morphologically characterized by a number of tests the results of which are shown in Table III below:

TABLE III

Morphological Characterization of Thermophilic Microorganisms Isolated from the Samples

| Test | ATCC No. 31068 | 31069 | 31070 | 31071 | 31072 | 31073 | 31074 | 31075 | 31076 | 31077 |
|---|---|---|---|---|---|---|---|---|---|---|
| Catalase | + | + | + | + | + | + | + | + | + | + |
| Growth at: | | | | | | | | | | |
| 35° C pH 6.0 | — | — | — | — | — | — | — | — | — | — |
| 35° C pH 7.0 | + | — | — | — | — | + | + | — | — | — |
| 60° C pH 6.0 | — | + | ++ | + | + | — | — | — | — | — |
| 60° C pH 7.0 | + | + | + | ++ | + | + | + | + | + | + |
| 65° C pH 6.0 | — | — | + | + | + | — | — | — | — | — |
| 65° C pH 7.0 | + | + | + | ++ | + | + | + | + | + | + |
| Nitrate Reduction | — | — | — | + | — | — | — | — | — | + |
| Starch Hydrolysis | — | — | — | — | — | — | — | — | — | — |
| 4% NaCl broth | + | — | — | — | — | + | + | + | + | — |
| Litmus milk | — | — | — | — | — | — | — | — | — | — |
| Gelatin liquefaction | — | — | — | — | — | — | — | — | — | — |
| Voges-Proskauer | — | — | — | — | — | — | — | — | — | — |
| Fermentation of: | | | | | | | | | | |
| Glucose | — | — | — | — | — | + | + | — | + | — |
| Arabinose | — | — | — | + | — | — | — | — | — | — |
| Maltose | — | — | — | — | — | + | + | — | + | — |

All of the above tests except where indicated were carried out at 55° C.

EXAMPLE II

This Example illustrates the production of α-1,6 glucosidases by thermophilic microorganisms of the present invention in liquid media containing a suitable source of carbohydrate.

Thermophilic microorganisms designated as ATCC numbers 31068, 31069, 31070, 31071, 31075 and 31076 were isolated from agar plate media in which samples were cultured, as previously described, and were propagated under aerobic conditions in a number of autoclaved aqueous nutrient media. Exemplary of such media are those having the compositions shown in Table IV below:

TABLE IV

Composition of Culture Media in Which Thermophilic Microorganisms Were Propagated

| Ingredients | Medium (Percent) A | B | C | D |
|---|---|---|---|---|
| Peptone | 1.0 | 1.0 | — | — |
| Tryptone | — | — | 0.5 | 0.5 |
| Yeast extract | — | — | 0.5 | 0.5 |
| Waxy maize starch | 0.5 | 0.5 | 0.5 | 0.5 |
| K₂HPO₄ . 3H₂O | 0.5 | 0.5 | — | — |
| NaNO₃ | 0.5 | 0.5 | — | 0.01 |
| CaCO₃ | 0.5 | — | — | — |
| CaCl₂ . 2H₂O | — | — | 0.01 | 0.01 |
| MgSO₄ . 7H₂O | 0.5 | 0.5 | — | 0.01 |
| CoCl₂ . 6H₂O | — | — | 0.01 | — |
| KCl | 0.05 | 0.05 | — | 0.01 |
| MnCl₂ . 4H₂O | 0.025 | — | — | — |
| FeSO₄ . 7H₂O | 0.001 | 0.001 | — | — |
| Maltose* | 2.0 | 1.0 | 1.0 | 1.0 |
| Maltitol* | — | 0.2 | — | — |
| pH before autoclaving | (6.8) | (6.7) | (6.7) | (6.7) |

*Autoclaved separately from the other ingredients

One loopful of culture growth from agar plate media in which the samples had been cultured was transferred aseptically to 250 ml shaker flasks each containing 50 ml of one of the autoclaved liquid media shown in Table I. The flasks were shaken at 150 rpm for four days at a temperature of 53° C. The contents of the flasks were then centrifuged and the supernatant assayed for starch debranching enzyme activity by the method previously described. The results of the assays indicated that all of the thermophilic microorganisms produced starch debranching enzymes as evidenced by the presence of amylose in the propagation broths.

EXAMPLE III

This Example illustrates the production of α-1,6 glucosidases by the thermophilic microorganisms propagated in liquid media containing maltose and varying amounts of amylopectin.

Cultures of the microorganisms set forth in Example II were inoculated into an autoclaved liquid medium having the composition shown in Table V below:

TABLE V

| Composition of Culture Medium | |
|---|---|
| Ingredient | Percent |
| Peptone | 1.0 |
| K₂HPO₄ . 3H₂O | 0.5 |
| NaNO₃ | 0.5 |
| CaCO₃ | 0.1 |
| MgSO₄ . 7H₂O | 0.05 |
| MnCl₂ . 4H₂O | 0.05 |
| KCl | 0.05 |
| FeSO₄ . 7H₂O | 0.001 |
| Maltose* | 2.0 |

TABLE V-continued

| Composition of Culture Medium | |
|---|---|
| Ingredient | Percent |
| pH before autoclaving | (7.0) |

*Autoclaved separately from the other ingredients.

Each of the six isolates was propagated in 10 ml aliquots of the above medium at a temperature of 53° C for two days. Each of these propagations were then used to inoculate 50 ml portions of the above medium to which 0.5, 1.75 and 3 percent substantially amylose free waxy maize starch had been added. Propagations were carried out in 250 ml shaker flasks shaken at 150 rpm for 5 days at a temperature of 53° C. Samples of the media were then tested for starch debranching enzyme activity with iodine-potassium iodide solution. The results of the experiment indicated that all six of the isolates produced starch debranching enzymes in media containing each level of the starch, but higher levels of starch debranching activity were noted in media containing the higher starch levels.

The terms and expressions which have been employed are used as terms of description and not of limitation, and it is not intended by the use of such terms and expressions to exclude any equivalents or the features shown and described or portions thereof, since it is recognized that various modifications are possible within the scope of the invention claimed.

What is claimed is:

1. A process for producing α-1,6 glucosidases comprising growing thermophilic microorganisms selected from the group consisting of the Bacillus genus, the Antinomycetales order and gram negative rod shaped microorganisms which produce α-1,6 glucosidases under aerobic conditions in an aqueous nutrient medium having present a carbohydrate selected from the group consisting of glucose, isomers of glucose, oligomers and polymers containing a glucose moiety or isomers of a glucose moiety and mixtures thereof and maintaining the medium at a suitable pH and a temperature of from about 45° to about 70° C to provide substantial growth of the microorganisms and production of α-1,6 glucosidase enzymes.

2. A process for producing α-1,6 glucosidases as defined in claim 1, wherein the thermophilic microorganisms are from the Bacillus genus.

3. A process for producing α-1,6 glucosidases as defined in claim 1, wherein the thermophilic microorganisms are from the order Actinomycetales.

4. A process for producing α-1,6 glucosidases as defined in claim 2, wherein the thermophilic microorganisms are ATCC numbers 31072, 31073, 31074, 31075, 31076 and 31077.

5. A process for producing α-1,6 glucosidases as defined in claim 3, wherein the thermophilic microorganisms are ATCC numbers 31069 and 31070.

6. A process for producing α-1,6 glucosidases as defined in claim 1, wherein the thermophilic microorganisms are ATCC numbers 31068 and 31071.

7. A process for producing α-1,6 glucosidases as defined in claim 1, wherein the temperature of the aqueous nutrient medium is maintained in the range of from about 50° to about 60° C during growth of the microorganisms.

8. A process for producing α-1,6 glucosidases as defined in claim 1, wherein the pH of the aqueous nutrient medium is maintained in the range of from about 5 to about 8 during growth of the microorganisms.

9. A process for producing α-1,6 glucosidases as defined in claim 9, wherein the pH of the aqueous nutrient medium is maintained in the range of from about 6.4 to about 7.2 during growth of the microorganisms.

10. A process for producing α-1,6 glucosidases as defined in claim 1, wherein the aqueous nutrient medium contains peptone.

11. A process for producing α-1,6 glucosidases as defined in claim 1, wherein the aqueous nutrient medium contains tryptone and yeast extract.

12. A process for producing α-1,6 glucosidases as defined in claim 1, wherein the aqueous nutrient medium contains maltose.

13. A process for producing α-1,6 glucosidases as defined in claim 1, wherein the aqueous nutrient medium contains maltitol.

14. A process for producing α-1,6 glucosidases as defined in claim 1, wherein the aqueous nutrient medium contains starch.

15. A process for producing α-1,6 glucosidases as defined in claim 1, wherein the thermophilic microorganisms are gram negative rod shaped microorganisms.

* * * * *